ize="5"># United States Patent [19]

Martins et al.

[11] 4,455,142

[45] Jun. 19, 1984

[54] METHOD OF COADMINISTERING AN ANTIGEN AND AN IMMUNOPOTENTIATOR

[75] Inventors: Agusto B. Martins; Alfred A. Amkraut, both of Palo Alto, Calif.

[73] Assignee: Alza Corporation, Palo Alto, Calif.

[21] Appl. No.: 338,328

[22] Filed: Jan. 11, 1982

Related U.S. Application Data

[63] Continuation-in-part of Ser. No. 171,902, Jul. 7, 1980, abandoned, which is a continuation-in-part of Ser. No. 91,119, Nov. 5, 1979, abandoned.

[51] Int. Cl.³ .................................................. A61M 13/00
[52] U.S. Cl. ................................................................ 604/890
[58] Field of Search ...................... 604/890, 891, 894; 424/19–24

[56] References Cited

U.S. PATENT DOCUMENTS

| | | | |
|---|---|---|---|
| 2,332,521 | 10/1943 | Masucci | 167/78 |
| 3,075,883 | 1/1963 | Scherr et al. | 167/78 |
| 3,135,662 | 6/1964 | Pope et al. | 167/78 |
| 3,452,135 | 6/1969 | Medveczky | 424/9 |
| 3,493,652 | 2/1970 | Hartman | 424/9 |
| 3,522,347 | 7/1970 | Ablondi et al. | 424/92 |
| 3,678,149 | 7/1972 | Prigal | 424/88 |
| 3,752,886 | 8/1973 | Munder et al. | 424/199 |
| 3,767,790 | 10/1973 | Guttag | 424/81 |
| 3,787,571 | 1/1974 | Higuchi | 424/239 |
| 3,814,097 | 6/1974 | Ganderton et al. | 128/268 |
| 3,837,340 | 9/1974 | Counter | 128/260 |
| 3,859,435 | 1/1975 | Bruzzese et al. | 424/94 |
| 3,937,815 | 2/1976 | Bruzzese et al. | 424/94 |
| 3,962,414 | 6/1976 | Michaels | 604/894 |
| 3,964,482 | 6/1976 | Gerstel et al. | 128/260 |
| 3,995,631 | 12/1976 | Higuchi et al. | 128/260 |
| 4,004,979 | 1/1977 | Avrameas et al. | 195/68 |
| 4,022,878 | 5/1977 | Gross | 424/1.5 |
| 4,057,685 | 11/1977 | McIntire | 536/18 |
| 4,122,158 | 10/1978 | Schmitt | 424/27 |
| 4,164,560 | 8/1979 | Folkman et al. | 424/22 |
| 4,166,800 | 9/1979 | Fong | 252/316 |

FOREIGN PATENT DOCUMENTS

25675 of 1909 United Kingdom.

OTHER PUBLICATIONS

Amkraut, Federation Proceedings, vol. 35, No. 3, p. 675, 1976.

*Primary Examiner*—Benjamin R. Padgett
*Assistant Examiner*—T. J. Wallen
*Attorney, Agent, or Firm*—Paul L. Sabatine; Edward L. Mandell

[57] ABSTRACT

A method is disclosed for potentiating the immune response of an animal. The method consists in administering an antigen and an immunopotentiator in effective low dose, at a controlled rate, and continuously to produce the desired immune response.

31 Claims, No Drawings

METHOD OF COADMINISTERING AN ANTIGEN AND AN IMMUNOPOTENTIATOR

CROSS-REFERENCE TO RELATED APPLICATIONS

This application is a continuation-in-part of United States patent application Ser. No. 171,902 filed on July 7, 1980 now abandoned, which application Ser. No. 91,119 filed on November 5, 1979 now abandoned, which application Ser. No. 171,902 and Ser. No. 91,119 are incorporated herein by reference, and benefit is claimed of their filing dates. This application and Ser. No. 171,902 and Ser. No. 91,119 all are assigned to the ALZA Corporation of Palo Alto, Calif.

FIELD OF THE INVENTION

The present invention pertains to enhancing the immunological competence of an animal. More particularly, this invention relates to both a novel and useful method for potentiating the immune response of an animal against an impeding infection, or a disease in progress. Specifically, the invention concerns a method comprising the continuous coadministering an antigen and an immunopotentiating agent at controlled rate over time for potentiating the immune response against said impeding infection or disease in progress.

BACKGROUND OF THE INVENTION

In the field of immunology, it is often necessary that more than one dose of an antigen be administered for producing an immunological response in an animal sufficient to ward off an impeding infection. Similar regimes have been advocated and used as an immunological program in the management of a disease in progress. In practice, multiple doses are administered because repeated interaction of immune system cells with antigen and necessary to build up the systems immune response. Further, multiple doses are required because the antigen is cleared from the site of administration or degraded by the animal too rapidly for permitting interaction between the cells and the antigen.

The prior art was attempted to increase both the persistence of the antigen and the vigor of the immune response, and avoid the use of multiple doses by administering an adjuvant with the antigen. The adjuvants used for the purpose consist of (a) substances like kaolin, gum tragacanth, tapioca, alum, aluminum hydroxide, calcium chloride and sodium alginate, oils and emulsions, which act as a depot for the antigens, as well as (b) substances like inactivated or attenuated bacteria, lipopolysaccharides, mucopeptides, other bacterial products possessing adjuvant properties, saponin, and synthetic organic compounds which potentiate the immune response by regulating active cell behavior. While the development and the use of adjuvants and depots represent a contribution to the prior art, serious disadvantages are associated with their use. For example, while one of the aims of using an immunologic adjuvant is to achieve a more durable immunity of a higher level than is obtained with a single dose of the antigen, in many instances a number of doses still are required to produce this intended result. In many instances the level of immunity achievable in a short time interval, for example seven to fourteen days, and it is inadequate for protecting from immediate threatening infections. In most instances the adjuvants themselves are a source of irritation that leads to severe inflammation. The prior art method of administration also exposes an unknown amount of both antigen and adjuvant, the latter often having adverse properties, to direct contact with local tissue; with the resulting duration and severity of the ensuing inflammatory response being therefore highly variable. Also, it is not known to the prior art that such materials could be administered and be effective in low amounts delivered at a controlled rate and continuously over a prolonged period of time. Currently, the use of depots, which are intended to function as an in vivo repository for an antigen, is replete with shortcomings. That is, depots do not keep their integrity and accordingly they do not maintain a predictable repository effect. By losing their integrity, they allow large numbers of inflammatory cells to accumulate at the depot site thereby producing unwanted irritation and often granulomatous lesions. Depots previously known to the art are made of materials that spread and diffuse throughout the area in which they are injected and they are not conducive for the controlled release of antigens over time. Also, depots are not immunopotentiators as they merely supply an antigen and they do not stimulate T-cells, B-cells, NK-cells, and the like.

It will be appreciated by those versed in the art and from the above presentation that if a method is made available for delivering an antigen and immunopotentiator to enhance the immune response, which method is essentially free of the disadvantages of multiple doses and the disadvantages of depots as known to the prior art, such a method would represent a valuable contribution to the art. Likewise, it will be appreciated by those versed in the art that if a method is made available which avoids giving rise to significant local inflammation and the like, such a method also would be a useful contribution to the art. Similarly, it will be appreciated that if a method is provided which accelerates the appearance of the immune response at protective levels, such a method would also be an improvement in the art.

OBJECTS OF THE INVENTION

Accordingly, it is an immediate object of the present invention to provide a novel and useful immunologic program for administering an antigen to a host which program is substantially free of the tribulations known to the prior art.

Another object of the present invention is to provide a method comprising the controlled and the continuous administration of an antigen and immunopotentiator over a predefined period of time for enhancing the immune response.

Yet another object of the invention is to provide a method comprising administering an antigen and immunopotentiator at extremely low and controlled rates that reduce or eliminate the incidence of irritation and inflammation previously associated with their use.

Still another object of the invention is to provide a method comprising dispensing an antigen and immunopotentiator which method allows for both the slow administration and the slow absorption within the host and attainment of greater prophylactic therapeutic immunological activity over time.

Yet still another object of the invention is to provide a method consisting essentially of dispensing an antigen and immunopotentiator from a delivery system that limits their contact with local tissues and which method allows for controlled release from the system that leads to slow absorption within a human host and attainment of enhanced preventative and therapeutic immunological activity.

Yet still another object of the present invention is to provide for the coadministering from a delivery device which serves as a reservoir, and houses therein an antigen and an immunopotentiator, said antigen and immunopotentiator on release from the device that maintains its physical and chemical integrity potentiates the immune response against an impending infection or a disease in progress.

Yet still another object of the present invention is to provide for the coadministration of an antigen and an immunopotentiator from a bioerodible matrix which possesses a controlled rate of bioerosion and serves as a reservoir at the loci of application, and houses therein the antigen and the immunopotentiator, said antigen and immunopotentiator on their release from the matrix at a controlled rate potentiating the immune response against an impending infection or a disease in progress.

These and other objects of this invention will become more apparent from the following detailed description and the accompanying claims.

SUMMARY OF THE INVENTION

This invention concerns the administration to an animal of an antigen and immunopotentiator for immunizing against an impending disease, or a disease in progress. The antigen and immunopotentiator are coadministered at a controlled and predetermined rate from a delivery system for a prolonged and defined period of time with an accompanying increase immunologic efficacy and a reduction in inflammatory responses. The delivery systems used for administering the antigen and immunopotentiator include diffusional, osmotic, elastomeric, mechanical or electrical facilitated device, noneerodible and erodible systems.

DETAILED DESCRIPTION OF THE INVENTION

In accordance with the practice of the present invention, it has now been found that an antigen and immunopotentiator can be continuously and simultaneously administered in extremely low to low doses over a prolonged period of time for enhancing the immune response with significantly improved effects over those obtained by single administrations of antigen and immunopotentiator.

Further, in accordance with the invention, the term antigen as used herein denotes naturally occurring and synthetic substances, representing, originating form, or simulating whole microorganisms, or their components, as well as materials of plant and animal origin, and their purified or simulated components. The antigens are capable of provoking an immune response. This consists of either the elaboration of antibody or the development of cell-mediated immunity. The antigens can be exogenous antigens, endogenous heterologus antigens, endogenous autologus antigens and endogenous homologus antigens. The term embraces materials such as toxoids, bacterial extracts, endotoxins, exotoxins, semi-particulate materials of viral origin, particulate materials of bacterial origin, foreign proteins, antigens bonded to an immunopotentiator and like materials that as a result of their coming in contact with the organs, tissues and systems of an animal body stimulate a prophylactic immune response, or aid in the management of a disease in progress.

The antigen may be in the form that is purified or partially purified and derived from bacteria, viruses, rickettsia or their products, or extracts thereof. The antigen may be a hydrolyzed or breakdown product prepared by acid digestion, extraction, or enzymatic digestion of the above, or it may be a synthetic product representing part of their structure. The antigens may be a poison or a venom derived from plants, insects and reptiles. The antigen may also be derived from animal tissues. The antigen will be in a physical state in which their toxic or virulent properties have been reduced or destroyed, and when administered into an animal will induce immunity by the production of antibodies or a cell mediated immune response. The antigens can be used singly or in combination, for example, multiple bacterial antigens, multiple viral antigens, multiple mycoplasmal antigens, multiple rickettsial antigens, multiple toxins, and the like. The antigen may be a dried powder, in an aqueous solution, in an aqueous suspension, or in an aqueous buffered solution.

Exemplary antigens of particular importance are derived from bacteria such as *B. pertussis, S. typhosa, S. paratyphoid* A and B, *C. diptheriae, C. tetani, C. botulinum, C. perfringens, B. anthracis, P. pestis, P. multocida, V. cholerae, N. meningitides, N. gonorrhea, H. influenzae, T. palladium,* and the like; antigens derived from viruses such as polio virus, adenovirus, parainfluenza virus, measles, mumps, respiratory syncytical virus, influenza virus, equine encephalomyeitis virus, hog chloera virus, Newcastly virus, fowl pox virus, rabies virus, feline and canine distemper viruses and the like; rickettsiae antigen such as epidemic and endemic typhus, and the spotted fever groups, and the like. Antigens are well known to the prior art in numerous references such as U.S. Pat. Nos. 3,149,036; 3,983,228; and 4,069,313; in *Essential Immunology,* 3rd Ed., by Roit, published by Blackwell Scientific Publications; in *Fundamentals of Clinical Immunology,* by Alexander and Good, published by W. B. Saunders; and in *Immunology,* by Bellanti, published by W. B. Saunders.

The term immunopotentiator, as used for the purpose of the present invention, generically embraces pharmaceutically acceptable and thermapeutically acceptable and active naturally occurring and synthetic materials, which on their release, concomitantly with an antigen by a delivery system to a host, potentiate the production of an antibody response or the development of cell-mediated immunity to the accompanying antigenic material. The immunopotentiator is a pharmaceutically active agent that acts in concert with the antigen with the object of potentiating the immune response so that a greater amount of antibodies or immunoactive cells are produced, the interval of achieving protection is reduced, a lesser quantity of antigen is required. The immunopotentiators possess pharmacological activity for potentiating the immune system by acting directly on macrophages to increase their activity, by increasing T-cell response, by increasing B-cell response, by increasing NK-cell response, by increasing complement activity, and the like.

Exemplary immunopotentiators that can be used according to the mode and manner of the invention include: lipopolysaccharides (LPS) extracted from gram-negative bacteria such as *Bordetella pertussis* or *Escherichia coli,* immunopotentiators obtained from anaerobic coryneforms, water soluble immunopotentiators obtained from the cell wall of bacteria, especially from Calmette-Guerin bacillus, (BCG), immunopotentiators especially cord-factor extracted from mycobacteria, peptidoglycans, peptidoglycans containing an arabinoglactin, peptidoglycolipids containing alanine, glutamic and diamino pimelic acids, water-soluble immunopotentiators (WSA) isolated from the cell walls and whole bacteria, e.g., of the species *M. smegmatis,* mucopeptides, immunopotentiators obtained from *Bacillus substilis, Saccharomyces cerevisiae, Listeria monocytogenes, Escherichia coli,* immunopotentiating proteins of animal origin, immunopotentiating glycopeptides, immunopotentiating polysaccharides, N-acetlyglucosamine, N-acetyl-muramyl-L-alanyl-D-isoglutamine, lipid A, lysolecithin analogues, polyanions, poly 1: C, poly A: U, poly A: poly U, saponin, levamisole, tilorone, lentinan, thymic factor, and other immunopotentiators prepared synthetically or derived from the endocrine or derived from the lymphoid or from the reticuloendothelial systems, or otherwise found in animal organisms, and the like metabolizable pharmaceutically acceptable immunopotentiators. The immunopotentiators are known to the art and the immunological terms used herein are in accord with conventional usage and art accepted definitions in *Immunological Adjuvants,* Report of WHO, Geneva, 1976; *Biochemical and Biophysical Research Communication,* Vol. 59, No. 4, pages 1317 and 1325, 1974; *Chemical Abstracts,* Vol. 88, 136980a, 1978; *Bibliotheca Tuberculosea,* Vol. 10, pages 130 to 148, 1956; *The Antigens, Vol.* 4, pages 369 to 428, 1977; *Immunopharmacology,* Vol. 3, Ch. 14, Hadden, Delmonte and Oettgen, 1977; and *Fundamentals of Clinical Immunology,* by Alexander and Good, 1977.

In the practice of this invention, a pharmaceutically acceptable carrier optionally may be used for administering the antigen and the immunopotentiator from the delivery system to a host. The carriers, when used, are transporting vehicles, they are both physiologically and pharmacologically inert, and they are devoid of immunopotentiating activity. Typical inert, nontoxic carriers include water, saline, balanced salt water solution and phosphate buttered saline. The antigen and the immunopotentiator are administered by the present invention oil-free and emulsion-free thereby providing improved immunological therapy, without causing local or systemic irritation to the recipient animal as caused by the prior art method of administration.

The term host as used herein denotes an animal, pices, avian, or reptile. The term animal includes warm-blooded mammals such as humans; farm animals such as sheep, cattle and goats; household animals such as dogs and cats; sport animals such as horses; laboratory animals such as mice and rats; and zoo animals. The term avians includes birds such as chickens and turkeys.

The phrase "a prolonged period of time" as used herein denotes a prolonged period including delivery periods of at least 1 day, and periods up to 380 days such as 1 day to 380 days, preferably 1 to 180 days inclusive, with a preferred period of 1 day to 72 days, a more preferred period of 1 day to 28 days, and a presently preferred period of 1 to 14 days. Periods of intermediate duration are included in the phrase. The prolonged period of time also includes the time needed to provide an adequate protection against an impending disease and it also can correspond to the period of time a threat of an impending infection exists, or a disease is in progress. The prolonged period also includes a pretreatment period. This period comprises the continuous administration of the antigen and immunopotentiator prior to exposure of a threating infection for 1 to 90 days, and more preferably for 14 to 45 days before said exposure. The expression "a threat of impending infections" denotes an advancing or anticipated epidemic such as chlorea, influenza, poliomyelitis, or rubella; childhood infections such as cytomeglovirus, measles, diptheria, poliomyelitis, mumps or rubella; infections prevalent in an environment into which the animal is about to enter such as diseases of the tropics including typhoid, cholera, paratyphoid, shigellosis and malaria; infections to which the animal may have been accidentally exposed such as tetanus, rabies and gangrene; diseases caused by organisms found abundantly in the environment but infections mainly to a comprised host such as pneumococcal pneumonia, pseudomonas and bacteroides infections, and the like. The expression "a disease in progress" denotes a disease such as herpes simplex, rabies, hepatitis, malaria, and the like.

The antigen-immunopotentiator composition can be administered in controlled and continuous dosage amounts for producing local and systemic immunization. The routes of administration include the conventinal routes such as intramuscular, subcutaneous, intraperitoneal, nasal, ocular, vaginal, and the alimentary tract including oral and ano-rectal administraction. For preferential local immunization, the route of introduction can be preselected accordingly. For example, oral administration is indicated for animals including humans where the purpose is to specifically immunize the gastrointestinal tract against diseases for which this is the major or exclusive route of infection, such as poliomyletitis, *E. coli enteritis,* salmonellosis, typhoid fever, shigellosis, cholera, coccidiosis, and similar diseases. The intramuscular route is indicated in humans for diptheria toxid, tetenus toxid influenza virus and the like, and in animals for Newcastle disease virus, anaplasma, blackleg and the like. Routes of administration are disclosed in *The Merck Veterinary Manual,* 4th Edition, 1973, published by Merck Co.; in Topley and Wilson's *Principles of Bacteriology and Immunolog,* Vol. 1 and 11, 1975, published by The Williams and Wilkins Co.

The expression "therapeutic delivery system" as used herein denotes systems or delivery means that can delivery an antigen and an immunopotentiator for producing antibodies and cell-mediated immunity in a preselected host. The systems are a means for delivering the antigen and the immunopotentiator, and the systems include reservoir means for housing the antigen and the immunopotentiator. Generally, the reservoir is an integral part of the system, or a delivery means can be connected to a reservoir housing the antigen and the immunopotentiator. The systems used do not allow for the total and complete direct access of cellular or homoral tissues and fluids of the animal to all the antigen and the immunopotentiator in the system. This limited contact and lack of interaction between the system and the agents housed therein with the tissues and fluids of the host animal coupled with the presently preferred, extremely slow administration of often potentially harmful immunopotentiators, significantly reduces and prevents incidence of local inflammation, or adverse biological responses such as fever or malaise. The systems can be used parenterally, subcutaneously, intramuscularly, orally, anorectally and the like. The systems also can be external systems which administer the antigen and immunopotentiator via a catheter to the host animal, for example through the catheter and a needle implanted subcutaneously or intramuscularly, and this will not cause local inflammation, or the system can be internally implanted biocompatible system that releases antigen at an effective and controlled immunological rate, for example 1 pg to 10 mg daily, more preferably 0.5 ng to 600 ng per hour.

The delivery systems can be bioerodible or non-erodible. Representative bioerodible systems include systems shaped like an implant of any geometric configuration, such as square, rectangular and the like, housing both the antigen and the immunopotentiator. The bioerodible systems are made of release rate controlling materials that act as a reservoir and house the antigen and immunopotentiator, and bioerode in the animal environment to non-toxic end products with concurrent release of antigen and immunopotentiator. The bioerosion of the bioerodible system is controlled by and inherent in the system, and this correspondingly controls the rate of release of active agents from the system, and it is essentially free of the influence of in vivo metabolism. The bioerodible system usually houses from 1 ng to 5 g of antigen and 1 ng to 5 g of immunopotentiator for release over a presently preferred 7 to 180 day day period. Representative bioerodible polymers suitable for manufacturing the immunological delivery systems include poly(carboxylic acid) as disclosed by Heller et al. in U.S. Pat. No. 3,811,444; polyvalent cross-linked polyelectrolytes as disclosed by Michaels in U.S. Pat. No. 3,867,519; polyesters, polylactic and polyglycolic acid as disclosed by Ramwell in U.S. Pat. No. 3,888,975; poly(ethylene oxide), poly(acrylamide), poly(vinyl pyrrolidone), poly(vinylimidazole), poly(vinyl alkyl ether) and poly(alkyl aldehyde) as disclosed by Zaffaroni in U.S. Pat. No. 3,971,367; poly(methacrylamide) and copolymers of acrylamide and methacrylamide as disclosed by Ramwell in U.S. Pat. No. 3,993,057; polyorthoesters and polyorthocarbonates as disclosed by Choi et al. in U.S. Pat. No. 4,138,344; poly(n-acetyl-glucosamines) as disclosed by Capozza in Belgium Pat. No. 825,367; and the like.

Representative delivery systems that maintain their physical and chemical integrity during the administration of an antigen and immunopotentiating agent include non-erodible systems such as the osmotic powered device disclosed by Theeuwes in U.S. Pat. No. 3,760,984; the osmotic dispensing device as disclosed by Theeuwes et al in U.S. Pat. No. 3,916,899; the electroosmotic pump as disclosed by Theeuwes in U.S. Pat. No. 3,923,426; the diffusion powered device as disclosed by Zaffaroni in U.S. Pat. No. 3,993,072; the osmotic miniture pump as disclosed by Higuchi in U.S. Pat. No. 3,995,631; the Harvard infusion pump, and the like pumps; and the infusion apparatus as disclosed by Buckles et al in U.S. Pat. No. 4,410,117. The devices include reservoir means and they can be implanted in the host, introduced into the host through body openings such as the ano-rectal route, the oral route, the vaginal route, or thay can be carried exteriorally by the host with a conduit that conveys the antigen and immunopotentiating agent from the devices to the host.

The device can house from 1 ng to 5 g of antigen and a like amount of immunopotentiating agent for administration subcutaneously, intramuscularly, and the like, over a prolonged period of time. The amount of antigen released from the above system is an effective amount for producing the immune response, usually from 1 pg to 10 mg per day, and more preferably from 0.5 ng/hr to 600 ng/hr. The amount of immunopotentiating agent release with the antigen generally ranges from 0.1 ng/hr to 600 ng/hr. Doses of antigen below these ranges may be administered as they often will lead to an immune response and continuous doses at this range can be used as they will usually maintain the response. The immune response, its intensity and the extent thereof produced by the mode and manner of the invention can be ascertained by measuring antibodies in the plasma by standard techniques. Additional techniques that can be used for ascertaining the nature of the provoked response include measuring active physiological reactions such as skin reactions following dermal, subdermal or intradermal administration, and by measuring the degree of inhibition of toxic response to or infection by the antigen due to immunization. These techniques and other acceptable techniques are known to the art in *Fundamentals of Immunology*, by Weiser et al, 1972, published by Lea & Febiger; *Immunology* by Bellanti, 1971, published by W. B. Saunders Company; *Practical Immunology*, by Hudson et al, 1976, published by Blackwell Scientific Publications; *Essential Immunology*, by Roitt, 1974, published by Blackwell Scientific Publications; and *Handbook of Experimental Immunology*, Second Edition, by Weir, 1973, published by Blackwell Scientific Publications, which are incorporated herein by reference.

The following examples are merely illustrative of the present invention and they should not be considered as limiting the scope of the invention in any way, as these and other examples and equivalents thereof will become apparent to those versed in the art in the light of the present disclosure, and the accompanying claims.

EXAMPLE 1

The immunopotentiating effect resulting from the continuous administration of the antigen lysozyme with an immunopotentiating lipopolysaccharide using an osmotic delivery device was measured and compared with the results obtained by a single subcutaneous injection of the lysozyme and the lipopolysaccharide. The antigen used was hen egg lysozyme, the immunopotentiator was lipopolysaccharide obtained from E. Coli, the animals were Swiss-Webster strain male mice weighing about 30 g, and the osmotic device was made according to U.S. Pat. No. 3,995,631. The device comprised an elastomeric reservoir made of butyl rubber surrounded by a layer of the osmotic solute sodium chloride and an outer layer of cellulose acetate.

The antibodies were assayed by a modified Farr assay. This method measures in the amount of radioactive antigen bound by the antibody contained in the test serum. The test was performed at an antigen concentration of 100 ng/ml by mixing 100 μl of antigen solution, 200 ng antigen/ml, with an equal volume of various dilutions of the test serum. The results are expressed an μg lysozyme bound per ml of the undiluted serum.

The study was designed to compare the immunopotentiating effects of the lipopolysaccharides given by a single injection in saline administered simultaneously with the antigen, with the immunopotentiating effects of the lipopolysaccharides given continuously with the antigen by the osmotic device. Five groups of mice (8 mice/group) were immunized as shown in accompanying Table 1. The mice were bled for antigody titration at 14, 28 and 60 days after initiation of immunization. In Table 1, LYS indicates lysozyme, LPS indicates lipopolysaccharide, ADM is method of administration, Sc indicates subcutaneously, 7D means 7 ways, 4W means 4 weeks, CD means continuous subcutaneous delivery, and the bracketed numbers indicates the measured range. The results in Table 1 show that LPS given with a single injection simultaneously with LYS is mainly effective in potentiating antibody production compared with continuous administration of LPS and LYS simultaneously by a drug delivery device. Further, analysis of the dose response in animals receiving continuous administration (Groups 11 to V) shows that a higher dose of antigen over a shorter period of time (Group 11) is very effective in achieving higher levels of antibody in a short period of time; while lower doses of antigen administered over a longer period of time are more effective in achieving a sustained high level antibody production which develops gradually.

soluble form via controlled continuous delivery, and its comparison with administration of the antigen in Freund's adjuvants is given in Table 2. In the table LY indicates lysozyme, LPS indicates lipopolysaccharide, 4W indicates 4 weeks, CD indicates continuous subcutaneous delivery, IFA indicates Freund's incomplete adjuvant, CFA indicates Freund's complete adjuvant, Group II and Group IV were given a single subcutaneous injection, and Groups I and III as osmotic device comprising a reservoir made of butyl rubber surrounded by a layer of osmotic solute sodium chloride and an outer layer of semipermeable cellulose acetate as described in Example 1 and in U.S. Pat. No. 3,995,631.

TABLE 2

| GROUP | GROUP Wt. µg | IMMUNIZATION | µg LYSOZYME BOUND/ml SERUM AT DAYS | | |
|---|---|---|---|---|---|
| | | | 14 | 28 | 60 |
| I | 234 | 10 µg Ly 4W CD | 0.87 [0.42–2.31] | 5.50 [0.6–9.4] | 1.13 [0.44–2.70] |
| II | 235 | 10 µg Ly in IFA | 0.73 [0.14–1.93] | 4.10 [1.58–7.77] | 4.45 [0.44–2.70] |
| III | 233 | 10 µg Ly + 100 µg 4W CD | 0.73 [0.43–2.93] | 4.10 [3.35–35.0] | 4.45 [1.09–8.20] |
| IV | 228 | 10 µg Ly in CFA | 1.87 [0.19–4.6] | 7.82 [2.5–1.8] | 5.13 [3.27–7.67] |

TABLE 1

| IMMUNIZATION DOSE IN µg | | | | µg ANTIGEN BOUND PER ml SERUM AVERAGE AT DAYS | | |
|---|---|---|---|---|---|---|
| GROUP | LYS | LPS | ADM | 14 | 28 | 60 |
| I | 200 | 50 | Sc | 0.63 [0.23–1.28] | 0.49 [0.07–0.76] | 0.23 [0.06–0.51] |
| II | 200 | 50 | 7D CD | 3.01 [2.1–6.0] | 2.15 [0.57–7.9] | |
| III | 10 | 100 | 4W CD | 1.12 [0.32–1.75] | 5.27 [0.07–12.3] | 2.22 [0.77–4.27] |
| IV | 10 | 10 | 4W CD | 1.55 [0.05–4.49] | 4.22 [0.07–1.53] | 1.1 [0.02–4.2] |
| V | 1 | 10 | 4W CD | 0.44 [0.02–1.34] | 1.09 [0.02–2.82] | 0.66 [0.02–1.42] |

EXAMPLE 2

In this example, the coadministration of lysozyme and lipopolysaccharide at a controlled and continuous rate is compared with Freund's adjuvant in animals. The lysozyme used was Sigma hen egg, the lipopolysaccharide was E. coli, the adjuvants were Freund's incomplete adjuvant at a dose of 0.1 ml emulsified with an equal volume of lysozyme in saline injected subcutaneously, the animals were Swiss-Webster-male mice weighing about 33 g, and continuous delivery was achieved by implanting an osmotic delivery device as described in Example 1 subcutaneously.

The study was designed to compare the amount of antibody produced by immunizing with lysozyme delivered at a controlled and continuous rate over a prolonged period of time both with and without immunopotentiating agent, with the amount of antibody produced in mice immunized with identical doses of the antigen incorporated in incomplete Freund's adjuvant, IFA, or complete Freund's adjuvant, CFA.

Four groups of mice, with 7 mice in a group, were immunized, and the animals bled for antibody titration on 14, 28 and 60 days after initiation. The potentiation of antibody production and memory cell generation by simultaneous administration of antigen and adjuvant in

EXAMPLE 3

In this example, the coadministration of the antigen tetanus toxoid and the immunopotentiator lipopolysaccharide administered for 4 weeks is compared with the results of single injection.

The assay of immunity was performed using the toxin challenge method as follows: graded doses of tetanus toxin diluted in PO$_4$ buffered saline containing 0.25% bovine serum albumin, BSA, were injected in 0.5 ml volume into each mouse subcutaneously. The mice were Swiss-Webster, female, weighing about 26 g. Mice were observed for symptoms of Tetanus, and death times were recorded. The periods of observation were as follows: 30–40 hours every 2 hours, 40–66 hours for every four hours, and 84 to 200 hours every 24 hours. The immunity was expressed as the number of minimum lethal doses of toxin required to kill immunized mice. The minimum lethal dose, MLD, is defined as the minimum doses of Toxim which kills all challenged mice in 200 hours or less.

The antitoxim titration was performed as follows: equal volume of toxin and doubling dilution of antisera were mixed, incubated at 37° C. for 1 hr. and injected subcutaneously in 0.5 ml volume into normal mice.

Three mice were tested at each dilution of antiserum. The potency of the test sera were assayed in comparison with the standard tetanus antitoxim, tested in parallel with the test sera. The antitoxin titrations were carried out at L+/400 levels, that is, the dose of toxin injected into each mouse was such that when mixed with 1/400 units of the standard antitoxin, the mixture killed the mice in 168 hours.

The experiment compares the immunopotentiating effect of lipopolysaccharide given simultaneously with antigen in a single injection with the immunopotentiating effect of lipopolysaccharide given simultaneously and continuously with antigen for four weeks. The lipopolysaccharide and antigen given subcutaneously and continuously was carried out with an osmotic device. The device comprised a reservoir made of butyl rubber, an intermediate layer of sodium chloride solute, and an outer wall of cellulose acetate. The device is described in U.S. Pat. No. 3,995,631. The antigen used, tetanus toxoid, permitted the use of an in vivo assay, with neutralization of toxin, for measuring the immunopotentiating effect.

Nine groups of mice (7/group) were immunized with a constant dose of tetanus toxoid (0.1 Lf=0.3 μg) mixed with graded doses of LPS. Five of the groups received the immunizing dose of LPS and antigen, or antigen alone by a single subcutaneous injection. The immunizing dose was administered to the other 4 groups for 4 weeks, 4W. Twenty-eight days after the initiation of immunization, all mice were bled for antitoxin titration. On day 33, 3 mice from each group were challenged with 20 or 50 minimum lethal doses of tetanus toxin, and on day 35, the remaining 4 mice from each group were challenged with 8, 20, 50 or 125 MLDs. The results for the immunopotentiationg effects of continuous administration of tetanus toxoid with or without lipopolysaccharide are given in Table 3. In the table, 4W means 4 weeks continuous administration with the osmotic device, Sc indicates subcutaneous, and Inj indicates injection.

added to the AlCl₃ solution drop by drop while holding the latter on a vortex mixer, with the pH adjusted to 6.8. The Diphtheria toxin used was obtained from Connaught Laboratories; the Diphtheria antitoxin was 100 I.U, International Units; and the guinea pigs were Hartley strain, female, weight about 290 g each.

The assay of immunity used the toxin challenge method as follows: Diphtheria toxin (0.005 Lf containing approximately 100 MRDs-minimal reacting doses) was injected intradermally in a volume of 0.2 ml, into each guinea pig and the reactions recorded at 6, 24, and 48 hours. The potency of the toxin was tested simultaneously in control non-immunized guinea pigs. The assay also used the antitoxin titration method as follows: equal volums of Diphtheria toxin and doubling dilutions of antisera were mixed, incubated at 37° C. for 1 hour, and injected intradermally in 0.2 ml volume in normal guinea pigs. The potency of the experimental sera was assayed in comparison with standard Diphtheria antitoxin, tested in parallel with the experimental sera.

A test for allergic reactions was performed by injecting intradermally 0.05, 1.0 and 10 Lf of Diphtheria toxoid in 0.2 ml volume and the skin reaction read at 6, 24, and 48 hours.

A test for local toxicity considered of measuring the skin thickness at the active sites at 24 hours, 7, 14 and 21 days following implantation. The sites of injection of the alum adjuvant were also palpated for evidence of reactions at the time noted. At day 38 and 60, the osmotic delivery devices were removed from the guinea pigs and the implant sites examined for gross evidence of toxicity. The sites of the injection of the alum adjuvant were similarly examined.

The studies of the example were designed to compare the immunopotentiating effect of Diphtheria toxoid absorbed on AlPO₄, with the immunopotentiating effect of soluble Diphtheria toxoid delivered continuously with and without lipopolysaccharides, LPS.

An absorbed Diphtheria vaccine was prepared so as to contain 50 Lf [150 μg] of Diphtheria toxoid and

TABLE 3

| GROUP | IMMUNIZATION | | | CHALLENGE DOSE OF TOXIN in MLDs (1) | | | | | CALCULATED LETHAL DOSE OF TOXIN (in MLD) | IU/ml (2) Pooled Serum |
| | TOXOID | LPS μg | Adm. | 1 | 8 | 20 | 50 | 125 | | |
|---|---|---|---|---|---|---|---|---|---|---|
| I | 0.1 Lf | NIL | | | | ⅓ | 0/4 | | >50 | 0.10 |
| II | | 0.2 | | | 0/3 | ⅓ | | | >50 | 0.10 |
| III | | 1.0 | 4W | | | | 0/3 | 0/4 | >125 | 0.24 |
| IV | | 5.0 | | | | | 0/3 | 2/4 | >125 | 0.40 |
| V | | NIL | | | 45 ± 8 | 48 ± 25 | | | <8 | |
| VI | | 0.2 | | | ⅓ | 164 ± 11 | | | 20 | 0.02 |
| VII | | 1.0 | Sc. | | ¾ | 65 ± 33 | | | <20 | |
| VIII | | 5.0 | Inj. | | | ⅓ | 62 ± 34 | | <50 | 0.03 |
| IX | | 20.0 | | | | | 33 ± 3 | 31 ± 2 | ~1 | |
| X | Unimmunized Control | | | 146 ± 30 | 38 ± 5 | 32 ± 3 | | | 1 | |

In Table 3 the footnotes are as follows:
(1) Response to toxin challenge: where all the mice died in of ≦200 hours challenge, the geometric death time (+SE) is given, otherwise the data is expressed as the number of mice dead in ≦200 hours/the number of mice challenged.
(2) International Units per ml of pooled serum, as compared to Connaught Laboratories Laboratory Standard.

EXAMPLE 4

This example pertains to coadministering Diphtheria toxoid and lipopolysaccharide compared with alum adjuvant in guinea pigs. The antigen used was Diphteria toxoid obtained from Connaught Laboratories. The alum adjuvant was aluminum phosphate adjuvant prepared as described by Levine et al. in *J. Immunol.* Vol. 75, pages 301 to 307, 1955. The alum adjuvant uses Na₂HPO₄ as the source of PO₄, the phosphate being AlPO₄ eqivalent to 0.65 mg Al per ml. Fifty Lf of Diphtheria toxoid is the maximum total dose that is usually given to children. 0.65 mg Al is the usual dose of alum adjuvant in vaccines. The maximum dose of Al permitted by the FDA is 0.85 mg Al. This vaccine was listed in guinea pigs at two dose levels: undiluted and diluted 1/50 in saline, by injecting 1.0 ml subcutaneously. The lower dose of the vaccine was expected to barely protect the guinea pigs against the diluted challenge dose of toxin.

For administration at a controlled and continuous rate, a soluble vaccine was prepared so as to contain 50 Lf of Diphtheria toxoid and 10 μg LPS in 0.175 ml. This vaccine was also listed at two dose levels, undiluted and diluted 1/50 in saline.

Six groups of guinea pigs (5/group) were used in this experiment. Four groups were immunized with the absorbed and the soluble (Toxoid+LPS) vaccine. The fifth group received 50 Lf toxoid alone at a controlled and continuous rate. The sixth group was used as a control. All the groups were bled on day 28 for antitoxin titration and skin tested with the toxin and the toxoid on day 29. Each of the immunized animals were given 4 skin tests as follows:

| Guinea pigs immunized with 1 Lf Toxoid | = | 0.005 Lf Toxin; 0.005 Lf Toxin + 0.05 Lf Toxoid; 0.05 Lf Toxoid; and 1 Lf Toxoid. |
|---|---|---|
| Guinea pigs immunized with 50 Lf Toxoid | = | 0.005 Lf Toxin + 0.05 Lf Toxoid; 0.05 Lf Toxoid; 1 Lf Toxoid; and 10 Lf Toxoid |

The control guinea pigs received 6 skin tests as follows: Toxin at 0.00004 Lf, 0.00002 Lf, 0.001 Lf, and 0.005 Lf; Toxoid and 1 Lf and 10 Lf. The skin tests were randomly distributed. On day 37 (8 days after the skin tests), guinea pigs immunized with 1.0 Lf toxoid were bled for antitoxin titration (secondary antibody production). On days 38 and 60, guinea pigs immunized with 50 Lf of toxoid were examined for local toxicity at the site of implantation or alum adjuvant injections.

The results of the skin tests are presented in Table 4. None of the guinea pigs immunized with 50 Lf of the toxoid developed reactions to the toxin, that is, they were immune. Of the 5 guinea pigs immunized with 1 Lf toxoid (+0.2 μg LPS) at a controlled constant delivery, 4 were not immune to the toxin challenge. The 5 guinea pigs immunized with 1 Lf toxoid in alum adjuvant, 1 was not immune, 1 was immune and three were partially immune. None of the immunized guinea pigs developed delayed hypersensitivity to the toxoid. A slight skin thickening was observed around the implanted osmotic pump in all groups in 24 hours. The osmotic pump is described in the previous examples and manufactured according to U.S. Pat. No. 3,995,631. Maximum skin thickening was observed on day 7. There was no palpable skin thickening around the minipump on day 14 or 21. The results are shown on Table 5.

TABLE 4

SKIN REACTIONS TO DIPTHERIA TOXIN AND TOXOID INJECTED INTRADERMALLY AND SERUM ANTIBODY TITERS 29 DAYS AFTER IMMUNIZATION IN GUINEA PIGS

| p | G.P. # | Immunization TOX | ADJ | ADM | Antibody on Day 28 I.U./ml | Reactions to Toxin[1] Dose of Toxin in Lf 0.00004 | 0.001 | 0.005 | 0.005 + 0.05 Txd | Rx to Toxoid[2] Dose of Toxoid in Lf 0.05 | 1.0 | 10.0 |
|---|---|---|---|---|---|---|---|---|---|---|---|---|
| 50 Lf | | | Nil | MP[3] | 0.85 | | | | — | — | 16 ± 2 | 24 ± 2 |
| | | | LPS 10 μg | MP | 2.0 | | | | — | — | 12 ± 3 | 19 ± 3 |
| | | | AlPO4 =0.654 mg AL | sc inj | 1.6 | | | | — | — | 12 ± 2 | 21 ± 2 |
| 1 Lf | 1 | | | | 0.04 | | | 35 | 30 | — | — | |
| | 2 | | | | 0.04 | | | 30 | 30 | — | — | |
| | 3 | | LPS | MP | 0.25 | | | — | — | 13 | 20 | |
| | 4 | | 0.2 | | 0.04 | | | 30 | 30 | — | — | |
| | 5 | | μg | | 0.04 | | | 25 | 25 | — | — | |
| 1 Lf | 1 | | | | 0.04 | | | 30 | 30 | — | — | |
| | 2 | | AlPO4 | sc | 0.25 | | | — | — | 10 | 20 | |
| | 3 | | 0.013 | inj | 0.04 | | | 15 | 15 | — | — | |
| | 4 | | mg | | 0.16 | | | — | 10 | 15 | 15 | |
| | 5 | | | | 0.04 | | | — | 10 | 20 | 20 | |
| Unimmunized controls | | | | | | 10 ± 0.4 | 24 ± 2 | 32 ± 3 | | — | — | |

In Table 4, the superscript 1 indicates the skin reactions to Diph. toxin measured at 48 hours. This is the optimum time for development of the reaction to Diph. toxin. The superscript 2 indicates skin reaction to Diph. toxoid measured at 6 hours. The six hour reactions (Arthus) are due to antibodies. All reactions to toxoid were negative at 24 and 48 hours; with delayed hypersensitive reactions reaching an optimum at 24 and 48 hours. The superscript 3 referring to the abbreviations MP which stands for the osmotic device indicates continuous delivery of 4 weeks duration. The figures represent the diameter in mm. (geometric means of two readings at right angles to each other) of the skin reaction. For groups I, II, III, and VI, only the average diameter ±SE of skin reactions in five guinea pigs is given. The abbreviations used in this table are defined in the previous examples, with the additional abbreviations as follows: I.U. means International Units, and Lf is a standard dose as disclosed in *Experimental Immunochemistry*, by Kabat and Meyer, pg. 13, 342, and 344–345, 1964, Charles C. thomas Publishers, and Dorland Medical Dictionary, 24th Ed., page 1648.

TABLE 5

Local Reaction In Guinea Pigs to Diphtheria Toxoid and LPS Delivered At Controlled, Continuous Rate

| | IMMUNIZATION | | | GROSS REACTION ON DAY | |
|---|---|---|---|---|---|
| GROUP | Txd | LPS | ADM | 7 | 14 |
| I | 50 Lf | Nil | CD | 8.57 ± 0.61 | 7.82 ± 0.33 |
| II | 50 Lf | 10 μg | CD | 8.95 ± 0.39 | 7.93 ± 0.20 |
| III | 1 Lf | 0.2 μg | CD | 8.45 ± 0.51 | 7.87 ± 0.51 |

In Table 5, Txd indicates the toxoid, LPS is Lypopolysaccharide, ADM indicates controlled, continuous delivery over a prolonged time of 7 and 14 days using the osmotic delivery device described in the previous examples. The thickness (in mm) is measured by folding the skin around the delivery means (average ±SE).

While the invention has been described and illustrated with reference to certain preferred embodiments thereof, those skill in the art will appreciate that various modifications, changes, omissions, and substitutions can be made without departing from the spirit of the invention.

I claim:

1. A method for potentiating the immune response of an animal, which method comprises administering an antigen and an immunopotentiating agent at a controlled rate from a delivery system that maintains its physical and chemical integrity and limits the contact of the animal from the antigen and the immunopotentiating agent until they are administered simultaneously to the animal continuously in an immunological effective amount of at least 0.5 ng/hr of the antigen, and an immunopotentiating effective amount of at least 0.1 ng/hr of the immunopotentiating agent for a prolonged period of time of at least one day up to 380 days, thereby potentiating the immune response of the animal.

2. The method for potentiating the immune response of the animal according to claim 1, wherein the antigen and the immunopotentiating agent are administered simultaneously and continuously oil-free for at least one day to the animal, and wherein the potentiation of the immune response is a cell medicated immune response, or the potentiation induces immunity by the production of antibodies in the animal.

3. The method for potentiating the immune response of the animal according to claim 1, wherein the method comprises administering the antigen and the immunopotentiating agent simultaneously and continuously to the animal to potentiate the immune response of the animal against an impending infection or a disease in progress.

4. The method for potentiating the immune response of the animal according to claim 1, wherein the method comprises administering the antigen and the immunopotentiating agent from a delivery device parenterally placed in the animal and the antigen and the immunopotentiating agent are administered for a prolonged period of time up to 180 days.

5. The method for potentiating the immune response of the animal according to claim 1 wherein the method comprises administering the antigen and the immunopotentiating agent from an external delivery system through a conduit parenterally to the animal for potentiating the immune response.

6. The method for potentiating the immune response of the animal according to claim 1 wherein the method comprises a single application in the animal of the delivery system housing the antigen and the immunopotentiating agent which are administered to the animal over a prolonged period of 1 to 180 days from the system that limits contact of the animal tissues and fluids from the antigen and the immunopotentiating agent until they are administered to the animal.

7. The method for potentiating the immune response of the animal according to claim 1 wherein the delivery system houses an immunopotentiating agent that is a member selected from the group consisting of a lipopolysaccharide, lipopolysaccharide endotoxin, mycobacteria, nucleic acid, polynucleotide, peptidoglycans, glycopeptides, polysaccharides lysolecthin, polyanions, levamisole, tilorone, lentinan and thyme factor.

8. The method for potentiating the immune response of the animal according to claim 1 wherein the delivery system is an osmotic system and the animal is a warm-blooded animal.

9. The method for potentiating the immune response of the animal according to claim 1 wherein the delivery system is a diffusional system and the animal is a warm-blooded animal.

10. The method for potentiating the immune response according to claim 1 wherein the animal is a warm-blooded animal and the antigen is administered in an immunologically effective amount of 1 pg to 10 mg daily.

11. The method for potentiating the immune response according to claim 1 wherein the animal is a warm-blooded animal and the antigen is administered to the animal at the rate of from 0.5 ng to 600 ng per hour.

12. The method for potentiating the immune response of the animal according to claim 1, wherein the animal is a warm-blooded animal and the immunopotentiating agent is administered in an immunologically effective amount of 1 pg to 10 mg daily.

13. The method for potentiating the immune response of the animal according to claim 1 wherein the antigen is a member selected from the group consisting of plant, animal, bacterial, viral and rickittsial antigens.

14. The method for potentiating the immune response of the animal according to claim 1 wherein the antigen is a member selected from the group consisting essentially of B. pertussis, S. typhosa, S. paratyphoid, C. diphtheriae, C. tetani, C. botulinum, C. perfringens, B. anthracis, P. pestis, P. multocida, V. chloerae, N. memigtides, N. gonorrhea, H. influenza, T. palladium, polio virus, adenovirus, parainfluenza virus, equine encephalomyetitis virus, hog chloera virus, Newcastle virus, fowl pox virus, rabies virus, feline and cannine distemper viruses, epidemic typhus, endemic lyptrus, and spotted fever antigen.

15. The method for potentiating the immune response of the animal according to claim 1 wherein the method immunizes the gastrointestinal tract against a disease that enters that tract.

16. The method for potentiating the immune response of the animal according to claim 1 wherein the delivery system administers the antigen and the immunopotentiating agent for 1 to 180 days intramuscularly into the animal.

17. The method for potentiating the immune response of the animal according to claim 1 wherein the delivery system administers the antigen and the immunopotentiating agent in a controlled and continuous amount subcutaneously to the animal.

18. The method for potentiating the immune response of the animal according to claim 1 wherein the delivery system comprising the antigen and the immunopotentiating agent limits the access of the cells and fluids of the animal until they are administered to the animal thereby lessening the incidence of inflammation consequent to the administration of the antigen and the immunopotentiating agent and their contact with the cells and the fluids of the animal.

19. A method for potentiating an antigen in need of potentiation, which method comprises administering the antigen and an immunopotentiating agent to an animal from a delivery system containing the antigen and the immunopotentiating agent, which delivery system maintains its physical and chemical integrity during the administration and limits the contact of the antigen and the immunopotentiating agent from the animal until they are coadministered continuously at a controlled rate, oil-free to the animal, in an effective amount of at least 1 pg/hr of antigen and 1 pg/hr of immunopotentiating agent for a prolonged period of time, up to 380 days, thereby potentiating the antigen in need of potentiation.

20. A method for potentiating an antigen in need of potentiation, which methods comprises administering the antigen and an immunopotentiating agent from a bioerodible delivery system containing the antigen and the immunopotentiating agent, which bioerodible delivery system bioerodes at a controlled rate and limits the contact of the antigen and the immunopotentiating agent from the animal until they are administered to the animal at a corresponding controlled rate in an effective amount consisting essentially of at least 0.5 ng/hr of antigen and 0.1 ng/hr of immunopotentiating agent over a prolonged period of time up to 380 days, thereby potentiating the antigen.

21. A method for potentiating the immune response of an animal, which method comprises administering an antigen and an immunopotentiating agent from a bioerodible delivery system formed of a non-toxic material that bioerodes at a controlled rate, contains the antigen and the immunopotentiating agent, and limits the contact of the antigen and the immunopotentiating agent from the animal until they are administered simultaneously to the animal at a correspondingly controlled and continuous rate, and wherein the antigen is administered in an immunologically effective amount of 1 pg/hr and the immunopotentiating agent is administered in a potentiating effective amount of 1 pg/hr for a prolonged period of time of at least one day up to 380 days, thereby potentiating the immune response of the animal.

22. The method for potentiating the immune response of an animal according to claim 21, wherein the bioerodible system administers the antigen and the immunopotentiating agent continuously and simultaneously for at least one day to the animal, and wherein the potentation of the immune response is a cell mediated immune response, and the potentiation induces immunity by the production of antibodies in the animal.

23. The method for potentiating the immune response of the animal according to claim 21 wherein the antigen and the immunopotentiating agent are administered continuously and simultaneously to the animal to potentiate the immune response against an impending infection or a disease in progress.

24. The method for potentiating the immune response of the animal according to claim 21, wherein the antigen and the immunopotentiating agent are administered for 1 day up to 180 days to potentiate the production of antibodies from a single application of the bioerodible delivery system that concomitantly limits contact of the animal tissues and animal fluids with the antigen and the immunopotentiating agent, with the antigen being administered at a controlled and continuous rate of 1 pg to 10 mg by the bioerodible delivery system and the immunopotentiating agent being administered at the controlled and continuous rate of 1 pg to 10 mg by the bioerodible delivery system.

25. The method for potentiating the immune response of the animal according to claim 21 wherein the bioerodible system housing the antigen and the immunopotentiating agent is a bioerodible polymer that limits their contact with the animal thereby reducing the incidence of inflammation in the animal, and the antigen is derived from a member selected from the group consisting of plant, animal, bacterial, viral and rickittsial origin.

26. The method for potentiating the immune response of the animal according to claim 21 wherein the antigen is a member selected from the group consisting essentially of B. pertussis, S. typhosa, S. paratyphoid, C. diphtheriae, C. tetani, C. botulinum, C. perfringens, B. anthracis, P. pestis, P. multocida, V. chloerae, N. menigtides, N. gonorrhea, H. influenza, T. pallidum, polio virus, adenovirus, parainfluenza virus, equine encephalomyetitis virus, hog chloera virus, Newcastly virus, fowl pox virus, rabies virus, feline and cannine distemper viruses, epidemic typhus, endemic typhus and spotted fever antigens.

27. The method for potentiating the immune response of the animal according to claim 21 wherein the bioerodible system is positioned intramuscularly in the animal.

28. The method for potentiating the immune response of the animal according to claim 21 wherein the bioerodible system is positioned subcutaneously in the animal.

29. The method for potentiating the immune response of the animal according to claim 21 wherein the bioerodible system is positioned parenterally in the animal.

30. The method for potentiating the immune response of the animal according to claim 21 wherein the immunopotentiating agent is a member selected from the group consisting of a lipopolysaccharide, lipopolysaccharide endotoxin, mycobacteria, nucleic acid, polynucleotide, peptidoglycans, glycopeptides, polysaccharides, lysolecthin, polyanions, levamisole, tilorone, lentinan, cord factor, thyme factor, proteins, peptides, synthetic, lymphoid, reticular and endothelial immunopotentiating agents.

31. The method for potentiating the immune response of an animal according to claim 21 wherein the bioerodible system limits the access of the cells and fluids of the animal to the antigenic agent and the immunopotentiating agent until they are administered to the animal thereby lessening the incidence of inflammation consequent to their administration and their contact with the cells and fluids of the animal.

* * * * *